(12) United States Patent
Riley et al.

(10) Patent No.: US 9,470,698 B2
(45) Date of Patent: *Oct. 18, 2016

(54) SYSTEMS AND METHODS FOR NON-FASTING LDL CHOLESTEROL ASSAYS

(71) Applicant: Polymer Technology Systems, Inc., Indianapolis, IN (US)

(72) Inventors: Timothy Riley, Indianapolis, IN (US); Aniruddha Patwardhan, Fishers, IN (US); Frank LaDuca, East Brunswick, NJ (US)

(73) Assignee: Polymer Technology Systems, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/961,634

(22) Filed: Dec. 7, 2015

(65) Prior Publication Data

US 2016/0084858 A1 Mar. 24, 2016

Related U.S. Application Data

(63) Continuation of application No. 13/874,971, filed on May 1, 2013, now Pat. No. 9,207,184.

(60) Provisional application No. 61/642,845, filed on May 4, 2012.

(51) Int. Cl.
| | |
|---|---|
| *G01N 33/92* | (2006.01) |
| *G01N 21/78* | (2006.01) |
| *C12Q 1/60* | (2006.01) |
| *G01N 33/52* | (2006.01) |
| *G01N 33/48* | (2006.01) |
| *G01N 21/77* | (2006.01) |

(52) U.S. Cl.
CPC ............. *G01N 33/92* (2013.01); *C12Q 1/60* (2013.01); *G01N 21/78* (2013.01); *G01N 33/525* (2013.01); *G01N 33/48* (2013.01); *G01N 2021/7759* (2013.01); *G01N 2021/7773* (2013.01)

(58) Field of Classification Search
CPC .. G01N 21/77; G01N 21/7769; G01N 21/78; G01N 33/48; G01N 33/92; G01N 33/525; G01N 2021/7773; C12Q 1/60
USPC ........... 436/63, 71, 164, 165, 166, 169, 170, 436/177, 178; 422/400, 420, 421, 422, 423, 422/82.05, 527, 534, 535; 435/11, 287.1, 435/287.7, 287.8, 287.9
See application file for complete search history.

(56) References Cited

U.S. PATENT DOCUMENTS

| | | | |
|---|---|---|---|
| 5,460,974 A | 10/1995 | Kozak et al. | |
| 6,342,364 B1 | 1/2002 | Watanabe et al. | |
| 6,794,157 B1 * | 9/2004 | Sugiuchi | C12Q 1/60 435/11 |
| 6,939,682 B2 * | 9/2005 | Tamura | C12Q 1/26 435/11 |
| 6,991,913 B1 * | 1/2006 | Wieland | G01N 33/92 435/18 |
| 7,087,397 B2 | 8/2006 | Anaokar et al. | |
| 8,357,502 B2 * | 1/2013 | Jumawid | G01N 33/92 435/11 |
| 9,207,184 B2 * | 12/2015 | Riley | G01N 21/78 |
| 2004/0126830 A1 * | 7/2004 | Shull | G01N 33/526 435/11 |
| 2005/0170447 A1 * | 8/2005 | Lawrence | G01N 33/526 435/11 |
| 2010/0099125 A1 * | 4/2010 | Yamaguchi | C12Q 1/26 435/11 |
| 2011/0223626 A1 | 9/2011 | Murakami et al. | |
| 2012/0282634 A1 * | 11/2012 | Hughes | G01N 33/538 435/7.25 |

OTHER PUBLICATIONS

Nauck et al. Clinical Chemistry, vol. 48:2, 2002, pp. 236-254.*
International Search Report in PCT Application No. PCT/US2013/039082 dated Sep. 27, 2013 (3 pages).
Nauck et al.; "Analytical and Clinical Performance of a Detergent-Based Homogeneous LDL-Cholesterol Assay: A Multicenter Evaluation," Clinical Chemistry, 2000; 46(4):506-514.
Siekmeier et al.; "Insufficient Accuracy and Specificity of Polyanion Precipitation Methods for Quantifying Low-Density Lipoproteins," Clinical Chemistry, 1990; 36(12):2109-2113.

* cited by examiner

*Primary Examiner* — Maureen Wallenhorst
(74) *Attorney, Agent, or Firm* — Haynes and Boone, LLP; Robert P. Ziemian

(57) ABSTRACT

In one embodiment, a test strip for testing for cholesterol-related blood analytes in whole blood includes a red blood cell separation layer, the red blood cell separation layer separating red blood cells from a blood sample applied to the test strip as the blood sample flows downward through the red blood cell separation layer. The test strip further includes a reaction layer receiving the blood sample from the red blood cell separation layer, the reaction layer including POE-POP-POE block copolymer, a surfactant, and a reflectivity changing reactant, the POE-POP-POE block copolymers solubilizing essentially only non-LDL cholesterol analytes, the non-LDL cholesterol analytes reacting with the reflectivity changing reactant in order to change a reflectivity of the blood sample.

13 Claims, 12 Drawing Sheets

SYSTEMS AND METHODS FOR NON-FASTING LDL CHOLESTEROL ASSAYS

CROSS-REFERENCE TO RELATED APPLICATIONS

This application is a continuation of U.S. patent application Ser. No. 13/874,971 filed May 1, 2013, now U.S. Pat. No. 9,207,184 issued Dec. 8, 2015, which claims the benefit of U.S. Provisional Application No. 61/642,845 filed May 4, 2012, which applications are hereby incorporated by reference to the same extent as though fully contained herein.

BACKGROUND

The measurement of low-density lipoprotein (LDL) cholesterol is an important health measure in the determination of health, especially cardiovascular health. It is desirable to have fast on-site measuring systems for LDL that does not require a laboratory or other facilities. In this way, health professionals may speak with patients immediately after a sample is taken, instead of having to wait days for test results to come back from a lab. In this way, the patient's history and status will be fresh in their mind and, therefore, lead to better results and analysis of patient health.

There are currently five known methods for quantifying low-density lipoprotein (LDL) cholesterol on a clinical chemistry analyzer in wet chemistry. Four of the methods are two-step reactions, where the first reagent reacts with all non-LDLs (HDL and VLDL) to produce a colorless product. Once the first reaction is complete, the addition of another reagent at a predetermined time then is utilized to quantify the remaining LDL. These methods appear to be incompatible with strip technology, as there is no way to reliably introduce multiple reagents at the critical timings needed. The final method, manufactured by Kyowa-Medex, claims to have a method where HDL and VLDL are blocked by sugar compounds (cyclodextrins), while LDL is selectively micellerized with specific surfactants and enzymes. Most importantly, the method claims to occur in one reaction which is complimentary for strip chemistry.

BRIEF SUMMARY

In one embodiment, a test strip for testing for cholesterol-related blood analytes in whole blood includes a red blood cell separation layer, the red blood cell separation layer separating red blood cells from a blood sample applied to the test strip as the blood sample flows downward through the red blood cell separation layer. The test strip further includes a reaction layer receiving the blood sample from the red blood cell separation layer, the reaction layer including POE-POP-POE block copolymer, a surfactant, and a reflectivity changing reactant, the POE-POP-POE block copolymers solubilizing essentially only non-LDL cholesterol analytes, the non-LDL cholesterol analytes reacting with the reflectivity changing reactant in order to change a reflectivity of the blood sample. Optionally, the test strip includes a spreading layer, oriented on top of the red blood cell separation layer. In one alternative, the POE-POP-POE block copolymer is selected from the list consisting of Pluronics L101: MW 3800, $POE_7$-$POP_{54}$-$POE_7$; Pluronics L121: MW 4400, $POE_5$-$POP_{68}$-$POE_5$; Pluronics P123: MW 5750, $POE_{20}$-$POP_{70}$-$POE_{20}$; and Pluronics F127: MW 12600; $POE_{106}$-$POP_{70}$-$POE_{106}$. Alternatively, the surfactant is Triton-X. The test strip may further include a secondary blood separation layer adjacent to the red blood cell separation layer, the secondary blood separation layer separating additional red blood cells from the blood sample. Optionally, the secondary blood separation layer further includes Dextran Sulfate. Alternatively, a molecular weight of the Dextran Sulfate is between 10K and 1000K. Alternatively, magnesium chloride (or magnesium ions) may be used in similar quantities. In another alternative, a molecular weight of the Dextran Sulfate is between 50K and 750K. Optionally, a molecular weight of the Dextran Sulfate is 500K. Alternatively, the POE-POP-POE block copolymer is Pluronics P123: MW 5750, $POE_{20}$-$POP_{70}$-$POE_{20}$. Optionally, a ratio of POE-POP-POE block copolymer to Triton-X is 10 parts POE-POP-POE block copolymer to one part Triton-X. In one alternative, a concentration of the Triton-X is at least 0.01%. In another alternative, a concentration of the Triton-X is at least 0.1%. In yet another alternative, a concentration of the POE-POP-POE block copolymer is at least 1%. Optionally, a concentration of the POE-POP-POE block copolymer is at least 2%. Alternatively, a concentration of the POE-POP-POE block copolymer is at least 3%. Optionally, a pH of the reaction layer is at least 5.4. Alternatively, a pH of the reaction layer is at least 6.8. In another alternative, a pH of the reaction layer is at least 7.4. Optionally, a pH of the reaction layer is 6.8. Alternatively, the blood separation layer includes D-23 borosilicate glass fiber impregnated with Phaselous Vulgaris (PHA-P) Lectins.

In one embodiment, a method of determining concentration of non-LDL cholesterol in a whole blood sample using a dry phase test strip includes contacting the whole blood sample with a blood separation layer of the test strip. The method further includes separating blood cells from the whole blood sample producing plasma and flowing the plasma through the blood separation layer to a test layer. The method further includes reacting a non-LDL fraction in preference to an LDL fraction and producing a color in the test layer substantially in proportion to a concentration of the non-LDL fraction in the sample. The method further includes measuring the color produced.

In another embodiment, a test strip for determining the concentration of LDL cholesterol in a sample of whole blood includes a test matrix (strip) having at least two stacks, a first stack of the at least two stacks for total cholesterol and a second stack of the at least two stacks for non-LDL. The first stack has reagents incorporated therein to produce a colorimetric response in proportion to the amount of total cholesterol in the samples. The second stack has reagents incorporated therein to produce a colorimetric response in proportion to the amount of non-LDL cholesterol in the sample. The test strip is configured to be read by a test meter, the test meter obtaining a value of non-LDL cholesterol from the second stack and subtracting the value of non-LDL cholesterol from a value of total cholesterol obtained from the first stack to yield a value of LDL cholesterol in the sample.

In another embodiment, a test strip and meter combination for determining the concentration of LDL cholesterol in a sample of whole blood includes a test strip. The test strip includes a test matrix (strip) having at least two stacks, a first stack of the at least two stacks for total cholesterol and a second stack of the at least two stacks for non-LDL. The first stack has reagents incorporated therein to produce a colorimetric response in proportion to the amount of total cholesterol in the samples. The second stack has reagents incorporated therein to produce a colorimetric response in proportion to the amount of non-LDL cholesterol in the sample. The combination includes a test meter configured to read the test strip. The test meter is configured to obtain a value of non-LDL cholesterol from the second stack and subtract the value of non-LDL cholesterol from a value of total cholesterol obtained from the first stack to yield a value of LDL cholesterol in the sample.

In another embodiment, a method of measuring LDL cholesterol from a human subject providing a blood sample includes providing a dry test strip and receiving the blood sample at the dry test strip. The method includes separating red blood cells from the blood sample in a first layer of the dry test strip and reacting non-LDL cholesterol in the blood sample in a reaction layer. The method includes producing a color change proportional to the non-LDL cholesterol and measuring the color change to determine a non-LDL cholesterol amount in the blood sample. The method includes subtracting the non-LDL cholesterol amount from a total cholesterol amount in the blood sample to yield an LDL cholesterol amount for the blood sample. Optionally, the blood sample is from an individual who has not fasted, and the resulting LDL cholesterol amount is more accurate than the Friedwald equation. Alternatively, a slope of a curve used to determine the non-LDL cholesterol is between 0.90 and 1.10. Optionally, VLDL cholesterol is not measured as LDL cholesterol. Alternatively, a reaction layer includes a POE-POP-POE block copolymer, a surfactant, and a reflectivity changing reactant, wherein the reacting includes solubilizing essentially only non-LDL cholesterol analytes, the non-LDL cholesterol analytes reacting with the reflectivity changing reactant in order to change a reflectivity of the blood sample. Optionally, the POE-POP-POE block copolymer is selected from the list consisting of Pluronics L101: MW 3800, $POE_7$-$POP_{54}$-$POE_7$, Pluronics L121: MW 4400, $POE_5$-$POP_{68}$-$POE_5$; Pluronics P123: MW 5750, $POE_{20}$-$POP_{70}$-$POE_{20}$; and Pluronics F127: MW 12600; $POE_{106}$-$POP_{70}$-$POE_{106}$. In one alternative, the surfactant is Triton-X. Optionally, the method includes spreading the blood sample with a spreading layer, oriented on top of the first layer. In one alternative, the method further includes reacting the blood sample in a total cholesterol reaction layer, the total cholesterol reaction layer oriented to receive a portion of the blood sample from the spreading layer; producing a color change proportional to a total cholesterol; and measuring a color change to determine the total cholesterol amount in the blood sample. Optionally, the test strip includes a secondary blood separation layer adjacent to the red blood cell separation layer, the secondary blood separation layer separating additional red blood cells from the blood sample, where the secondary blood separation layer further includes Dextran Sulfate. Alternatively, the first layer includes D-23 borosilicate glass fiber impregnated with Phaselous Vulgaris (PHA-P) Lectins.

BRIEF DESCRIPTION OF THE DRAWINGS

FIG. 3b shows the linearization of the % R graphs using Kubelka-Munk equation of FIG. 3a;

DETAILED DESCRIPTION OF THE INVENTION

Figure 1A:
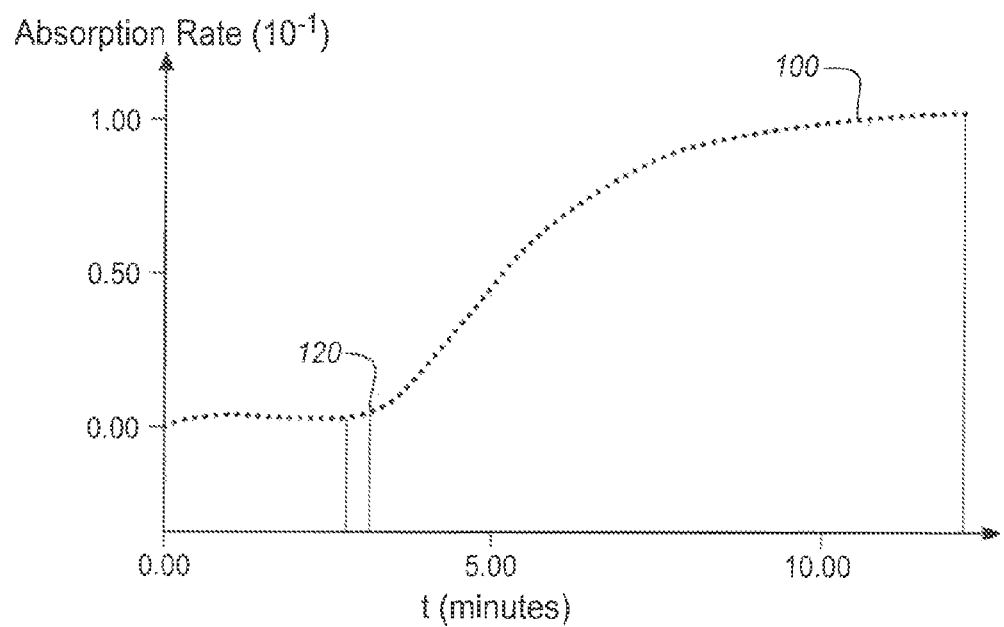
FIGS. 1a and 1b show reaction kinetics data collected on a clinical chemistry analyzer (for example Roche Cobas Integra 400+) for a two reagent system utilizing Pluronics L121 and Triton X-100 to demonstrate selectivity for non-LDL Cholesterol.

Certain terminology is used herein for convenience only and is not to be taken as a limitation on the embodiments of a non-fasting LDL test strip. In the drawings, the same reference letters are employed for designating the same elements throughout the several figures.

The words "right," "left," "front," and "back" designate directions in the drawings to which reference is made. The words "inwardly" and "outwardly" refer to directions toward and away from, respectively, the geometric center of the non-fasting LDL test strip and designated parts thereof. The terminology includes the words above specifically mentioned, derivatives thereof, and words of similar import. The drawings are proportional.

Like reference numerals designate like or corresponding parts throughout the various views and with particular reference to each of the FIGS. as delineated below.

In brief, a non-fasting LDL assay has been created in which all non-LDL is reacted and measured and then subtracted from a total cholesterol amount in order to determine the LDL concentration. The assay is based on providing a chemistry that solubilizes all cholesterols other than LDL for measurement. In some embodiments, the chemistry includes Triton X-100 and Pluronics P123. In some embodiments, an initial incomplete precipitation step is included to improve the resulting removal of LDL. In some embodiments, this initial incomplete precipitation is provided and, in order to enhance the selectivity of Triton X-100 and Pluronics P123, includes additionally adding Dextran Sulfate/$Mg^{+2}$, which brings the bias of the assay within 10%. The assay is referred to as non-fasting since the assay is specific enough not to have the accuracy negatively affected by the presence of Chylomicrons. In this embodiment the ability of the assay to isolate lipoprotein density classes without the use of standard ultracentrifugation is unique resulting from the selective solubilization of lipoprotein particles differing in densities with the exclusion of LDL.

As mentioned above, it is desirable to have a direct LDL measurement technology that does not rely on estimate-based calculations from total cholesterol. Since it would be desirous to have such an assay, Applicants analyzed the Kyowa-Medex patent. The author of the Kyowa-Medex patent (U.S. Pat. No. 6,794,157 B1), Hirochi Sugiuchi, calls out a polyoxyethylene-polyoxypropylene (POE-POP) triblock copolymer, Pluronics L121, as the crucial component for directly measuring LDL in an aqueous two reagent based system ("Wet Chemistry") applied to Roche's clinical chemistry analyzer like Integra 917, Modula P and Cobas Integra 400+. Wet Chemistry systems vary significantly from dry test strip systems in that in Wet Chemistry systems reactants can be added at certain times and therefore timing can be carefully controlled. Furthermore, in Wet Chemistry systems all reactants tend to be mobilized and active in contrast to dry test strips with may require greater concentrations of reagents due to degradation and other mobilization issues. Research into this component demonstrated that it had no selectivity for LDL on its own. The patent briefly mentions the use of several co-surfactants (one such example being the use of Emulgen L40), alpha-sulfated cyclodextrins, and enzymes, leading to the initial belief of their relatively minor role in the reaction. However, after the lack of success screening Pluronics L121 for LDL selectivity in a two reagent format like Sugiuchi's, it became clear these additives were more crucial than previously thought. Moreover, it was found that Emulgen L40 (prepared by Kao Corporation) is not commercially available; and we believe Kyowa-Medex has exclusive rights to that co-surfactant. Applicants have repeatedly and thoroughly tested the methodology outlined in U.S. Pat. No. 6,794,157 B1; however, it is believed that proprietary methods and reactants were not disclosed or are not available to the public.

After an exhaustive search and screening attempt as described above covering many surfactants, enzymes, and sugar compounds, it became clear that the Kyowa-Medex patent was not easily reproducible. Some proprietary method was being excluded, which prevented another successful, one-step LDL assay from being created. However, some combinations of Pluronics L121 with Triton X-100, which is known to indiscriminately strip lipoproteins, yielded interesting results, in a two reagent, based system as observed on a clinical chemistry analyzer.

Figure 1B:
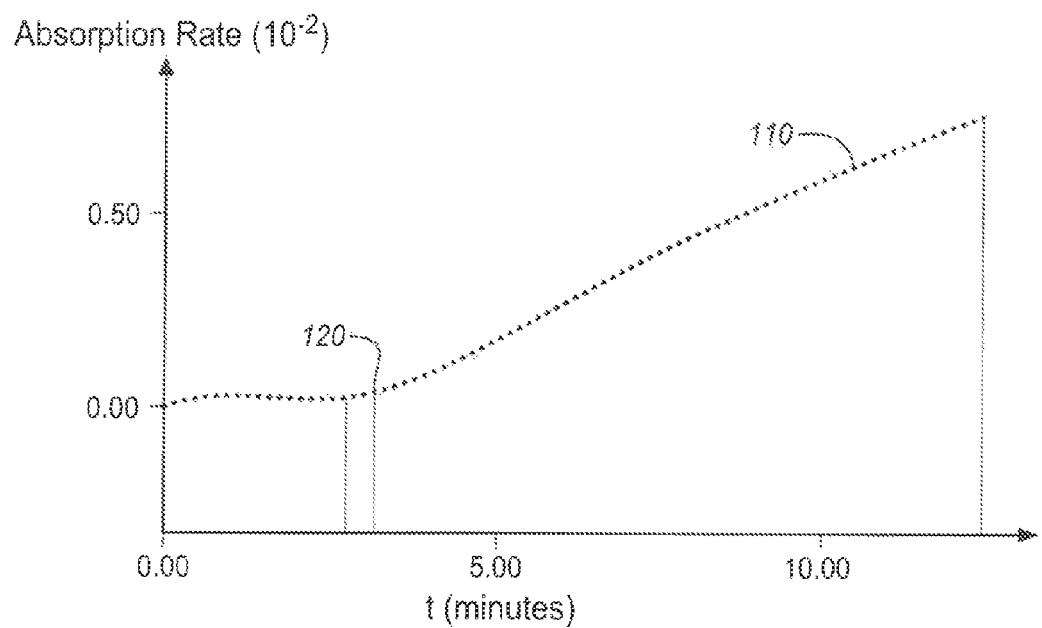

In an attempt to identify a test selective for LDL, that results in a dry test strip, a more fundamental approach was taken to fully understand the role of L121 and Triton X-100. A similar two reagent based ("Wet Chemistry") approach was initially employed. As can be seen from the reaction kinetics below (FIGS. 1a and 1b; data collected on clinical chemistry analyzer), the HDL (trend line 100) reacted at a much faster rate than the LDL fraction (trend line 110). In these graphs the sample is added at point 120. This result was greatly unexpected, as Triton X-100 traditionally is used as a general surfactant to solubilize all the lipoproteins and primarily used as a surfactant of choice for a total cholesterol assay. Therefore, the combination of a compound known to solubilize all lipoproteins in combination with a compound thought to solubilize only LDL actual leads to a result that all non-LDL is solubilized. FIGS. 1a (HDL) and 1b (LDL) show Absorbance vs. Time graphs of a TX100/L121 solution combined with an enzyme/MAOS N-Ethyl-N-(2-hydroxy-3-sulfopropyl)-3,5-dimethylaniline/4AAP (pH 6.8), sodium salt solution to achieve final surfactant solution 0.25% TX100/0.5% L121. This reagent then is combined with a sample at mark 120 and measurements are taken at defined intervals up to end of the reaction. Note that the amount of Triton-X utilized is much lower than typically used to solubilize all lipoproteins. In short, in an attempt to follow U.S. Pat. No. 6,794,157 B1 to replicate the LDL assay and achieve a direct LDL measurement, a much different result was reached. Per the patent examples listed in Table 1, the authors employed 0.2% Pluronic L121 and 0.1% Emulgen 911 to achieve high LDL to HDL selectivity. However, upon replicating the same concentrations in our laboratory, we observed a high HDL-to-LDL selectivity, which is opposite to the claim of U.S. Pat. No. 6,794,157 B1. Titrating different combination of Emulgen 911 and L121 only gave the same selectivity (high HDL:LDL) and sometimes no selectivity contrary. This reversal of selectivity prompted the testing with TX-100 and other octylphenols and nonylphenols.

Originally, it was thought that this would lead to an assay that would react only LDL. Instead, the test results show the potential for a test that reacts all constituents other than LDL. While this is the opposite of the originally desired reaction, an assay has been determined where all non-LDL is reacted and subtracted the value from a known total cholesterol value. This method, while not direct, still poses several advantages over the Friedwald equation. The largest inadequacy of the Friedwald equation is the estimation of VLDL to be assumed as ⅕ the concentration of triglycerides. This is not true for many people, and the Friedwald equation typically underestimates LDL for individuals who have not fasted. These issues would be resolved by measuring non-LDL(HDL+VLDL+CM), giving an LDL value identical to a direct LDL assay.

Figure 2A:
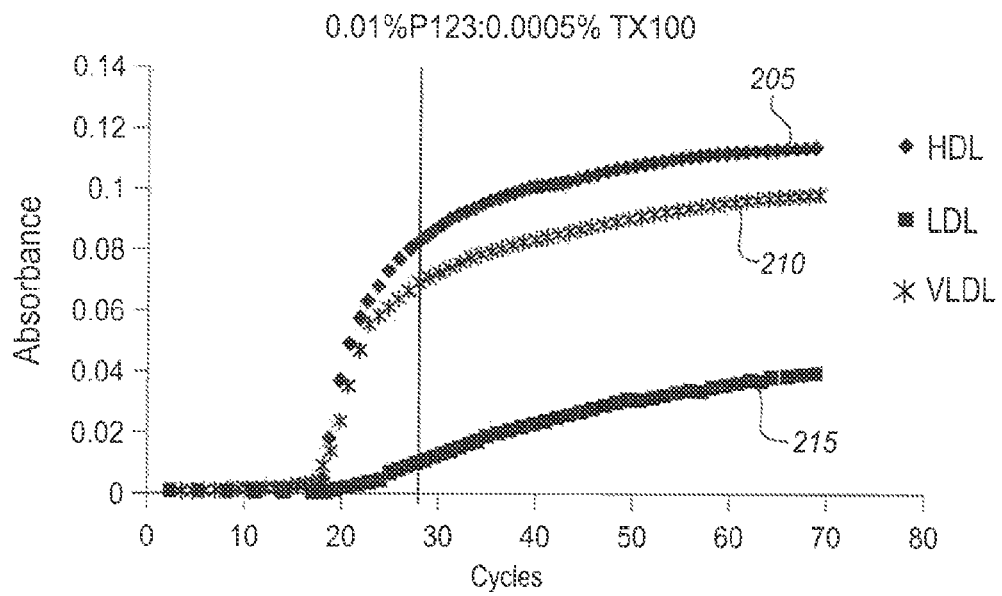
FIGS. 2a and 2b show a comparison of the HDL and LDL fractions reacting (kinetics) in a reagent based system with and without Triton X and Pluronics P123.
Figure 2B:
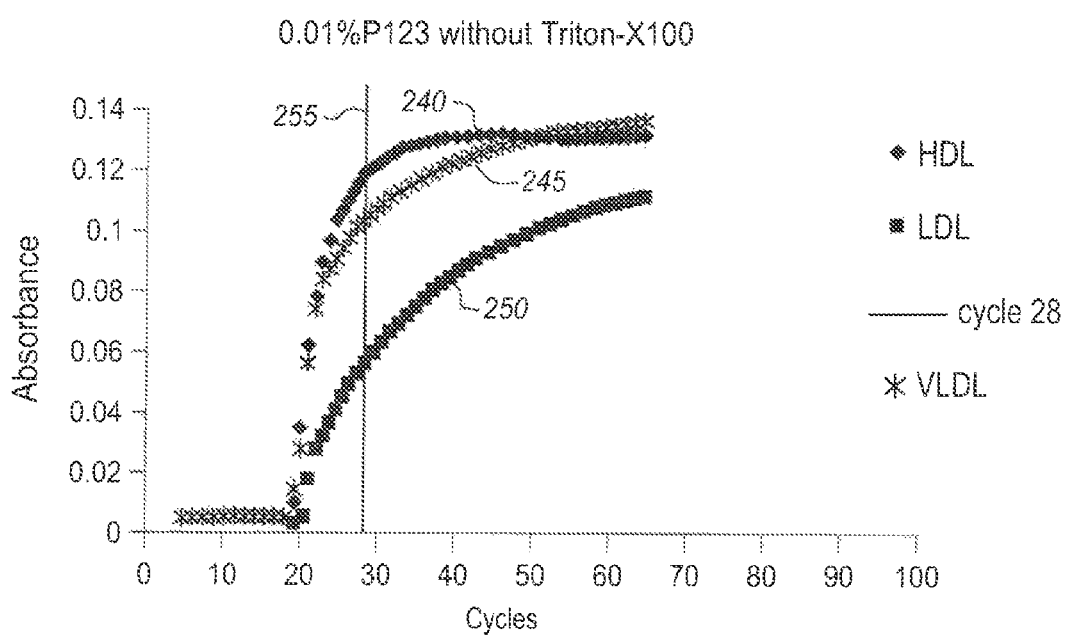

Pluronics L121 demonstrated surprising HDL selectivity when solubilized with Triton X-100. Therefore it was concluded that combinations of Triton X-100 and $POE_X$-$POP_Y$-$POE_X$ could yield high specificity for HDL and all non-LDL cholesterols. It was considered a worthwhile experiment to try different Pluronics series to attempt to increase this selectivity. In some embodiments, different Pluronics are optionally utilized including, but not limited to:

Pluronics L101: MW 3800, $POE_7$-$POP_{54}$-$POE_1$;
Pluronics L121: MW 4400, $POE_5$-$POP_{68}$-$POE_5$;
Pluronics P123: MW 5750, $POE_{20}$-$POP_{70}$-$POE_{20}$;
Pluronics F127: MW 12600, $POE_{106}$-$POP_{70}$-$POE_{106}$ The reagent was prepared by combining 0.7 ku Cholesterol Esterase, 0.5 ku Cholesterol Oxidase, 12 ku horseradish peroxidase in MOPS buffer with 0.58 mM 4-Amino antipyrine and 2.9 mM MAOS followed by the following concentrations of Pluronics (P123) and Triton X-100 mixtures. This reagent was tested on an automated clinical chemistry analyzer (namely, Roche's Cobas Integra 400+) to determine the selectivity. The table below shows the selectivity. Highest selectivity of ~15:1 HDL:LDL observed was at 10:1 P123:Triton X-100 ratio. Shown in FIGS. 2a and 2b is a comparison of the HDL and LDL fractions reacting under similar conditions as FIGS. 1a and 1b with a final surfactant concentration consisting of 0.01% P123/0.0005% TX100. Cycle 28, mark 255, indicates the reaction about 2 minutes after the addition of sample, denoting a possible time limit for a test strip reader, such as the CardioChek® assay. FIG. 2a shows the P123 Triton X-100 combination, showing HDL trend lines 205, LDL trend lines 215, and VLDL trend lines 210. FIG. 2b shows only P123 without Triton X-100 condition, showing HDL trend line 240, LDL trend line 250, and VLDL trend line 245. This clearly demonstrates selectivity for HDL over LDL.

TABLE 1

Selectivity and concentrations for P123 and Triton X-100.

| P123:Triton X-100 ratios and concentrations | HDL:LDL Selectivity |
|---|---|
| 1:1 | |
| 1%:1% | 1.17 |
| 0.1%:0.1% | 2.32 |
| 0.01%:0.01% | 2.57 |
| 3:1 | |
| 1%:0.33% | 1.84 |
| 0.1%:0.033% | 3.86 |
| 0.01%:0.0033% | 5.40 |

TABLE 1-continued

Selectivity and concentrations for P123 and Triton X-100.

| P123:Triton X-100 ratios and concentrations | HDL:LDL Selectivity |
|---|---|
| 6:1 | |
| 1%:0.165% | 6.28 |
| 0.1%:0.0165% | 9.65 |
| 0.01%:0.00165% | 5.29 |
| 10:1 | |
| 1:0.1% | 10.71 |
| 0.1%:0.01% | 14.82 |
| 0.01%:0.001% | 5.22 |
| 20:1 | |
| 0.1%:0.005% | 9.56 |
| 0.01%:0.0005% | 8.72 |

According to Table 1, the best concentration appears to be approximately 10:1 for "wet chemistry".

P123 is a larger, more hydrophilic POE-POP copolymer and was found to solubilize much easier than L121, allowing for greater concentrations and ratios to be tested. The selectivity for HDL to LDL is very high (10:1) at cycle 28 leading to the use of P123 as the most optimized surfactant of choice to use with Triton X-100 to selectively solubilize non-LDLs.

Therefore, embodiments of a reagent combination selective of non-LDL cholesterols include combinations of Triton X-100 and $POE_X$-$POP_Y$-$POE_X$. Optionally, these combinations include compounds of $POE_X$-$POP_Y$-$POE_X$ having a molecular weight ranging from 2,500 to 15,000. Optionally, the molecular weight is from 4,000 to 10,000. Optionally, the molecular weight is from 5,000 to 7,000. Optionally, the molecular weight of the $POE_X$-$POP_Y$-$POE_X$ is 5,750.

The "wet chemistry" protocol used to identify the properties of these surfactants was necessary to screen the many surfactants/ingredients tested. However, transfer to a dry test strip required re-optimizing concentration and ratios significantly. The two reagent based "wet chemistry" approach no longer served further purpose on a clinical analyzer. Originally, two reagent systems were of interest since in a dry test strip, multiple reagents cannot be added at various times to carryout various parts of the reaction. All reagents must be present in the test strip when the sample is applied. The more reagents required in a wet chemistry test, the greater chance that the reagents will interact effecting the efficiency of the test when they are all placed in a dry test strip and wetted simultaneously. Also, in the conversion to a dry test strip, typically a much higher concentration of reagents is needed.

In order to develop a working test strip system, in one embodiment, the test strip was arranged as follows. In a two reagent based system, the ratio of 10 parts P123 to one part Triton X-100 provided the best results, with the Triton X-100 concentration at 0.01%. In the previous Polymer Technology Systems, Inc. (PTS), total cholesterol assay, the Triton X-100 concentration is 0.1%. The reagents for dry test strip was prepared by impregnating Biodyne A from Pall with a solution of 241 ku/LCholesterol Esterase, 74 ku/L Cholesterol Oxidase, 232 ku/L peroxidase in MOPS buffer with 5 mM 4-amino antipyrene, and 40 mM MAOS (N-Ethyl-N-(2-hydroxy-3-sulfopropyl)-3,5-dimethylaniline, sodium salt) followed by the following concentrations of P123: Triton X-100 system. The sheet was dried in a constant temperature drying tunnel prior to preparing the dry test strips. A higher concentration of constituents is needed in test strips to obtain similar results as in wet chemistry environments. As a starting point for the non-LDL assay, the TX-100 concentration remained at 0.1% for a direct comparison to a total cholesterol strip. The enzyme concentration also was kept the same as that of the PTS total cholesterol reaction membrane. In order to maintain a 10:1 ratio, the P123 concentration was increased to 1%, and the pH was raised to 6.8. The reagent then was coated onto 0.45 μ Biodyne A membrane and dried at room temperature.

The non-LDL Biodyne was cast into single-analyte test strips using the following format:

TABLE 2

Shows an example of a Non-LDL according to currently described methodologies.

| | |
|---|---|
| Blood Spreading Layer | Petex |
| Blood Separation layer | Alhstrom 144 |
| Secondary Blood Separation Layer | Cytosep 1660 |
| Reaction Membrane | Non-LDL Reaction Membrane |

Figure 3A:
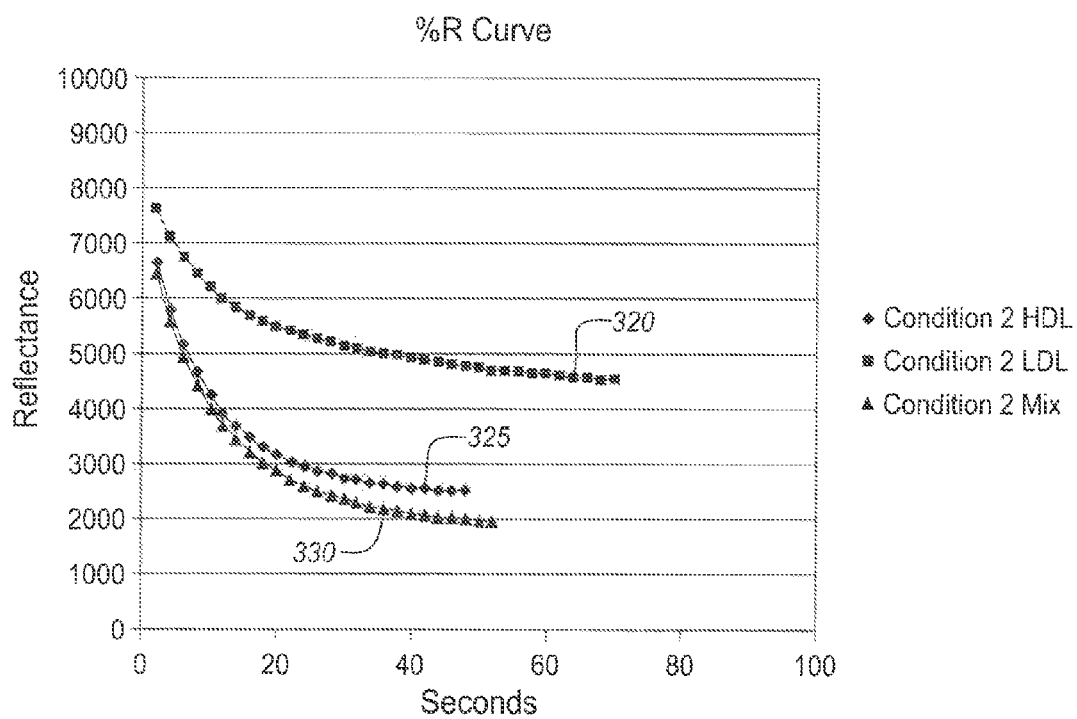
FIG. 3a shows the reaction kinetics in terms of percent reflectance (% R) and an experimental test (P123 and Triton-X)
Figure 3B:
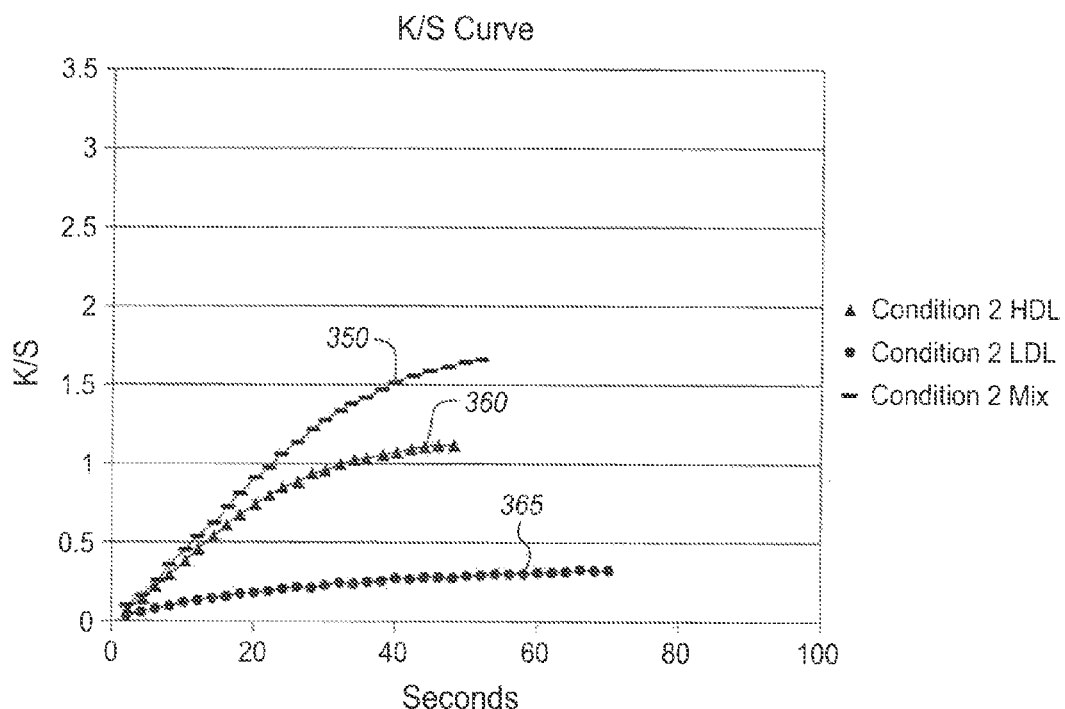

The strips then were tested with an HDL fraction (178 mg/dL), an LDL fraction (188 mg/dL), and a mixture of fraction (368 mg/dL) on meters that recorded percent reflectance (% R) as measured on a CardioChek® meter until reaction completion. FIGS. 3a and 3b show the % R and K/S, respectively, for an experimental test (P123 and Triton-X) of a sample showing HDL 325, 360, LDL 320, 365, and mixture of (HDL:LDL) 330, 350. Reflectance was converted to K/S units using Kubelka-Munk equation to form a linear relationship with respect to concentration (similar to absorbance) where the reduction in concentration is directly proportional to K/S reduction.

The results with the experimental strips containing P123 was very encouraging. The LDL and HDL fractions were approximately equivalent in concentrations (confirmed through another testing methodology, the Integra), and the mixture was about double the reaction of both of the individual fractions. The addition of the P123:Triton X-100 mixture drastically reduced the kinetic trace of the LDL fraction and the mixture, while only slightly inhibiting the HDL fraction. This suggests that the majority of the mixture reaction observed with P123 strips is composed of HDL. Similar results were observed with lipoprotein fractions of a reduced concentration. As the results show, the reflectivity created by an LDL fraction is reduced as compared to the reflectivity created by an HDL fraction of approximately equivalent concentration. The reflectivity is correlated to the amount of reacted fraction in the sample. The higher the reflectivity, the less analyte available for reaction. Therefore, a high reflectivity for the LDL fraction, as shown, is reflective of a low amount of LDL cholesterol available for detection. Since reflectivity is not linearly related to the concentration of an analyte, K/S plots are created, providing a linear relationship to the concentration of an analyte. For purpose of quantification and to determine observable diminished LDL reactivity only K/S plots will be used going forward.

The "wet chemistry" protocol used to identify the properties of these surfactants was necessary to screen the many surfactants/ingredients tested. However, transfer to a dry test strip required re-optimizing concentration and ratios significantly. The two reagent based "wet chemistry" approach no longer served further purpose on a clinical analyzer. In a wet chemistry approach, reagents may be added at the appropriate times. In contrast, such timing mechanisms are generally not possible in dry test strips, since the reagents must be pre-impregnated in the test strips. Furthermore, the concentration of reagents required in test strips is typically much greater, since reagents may be inactivated during the drying process.

Figure 4A:
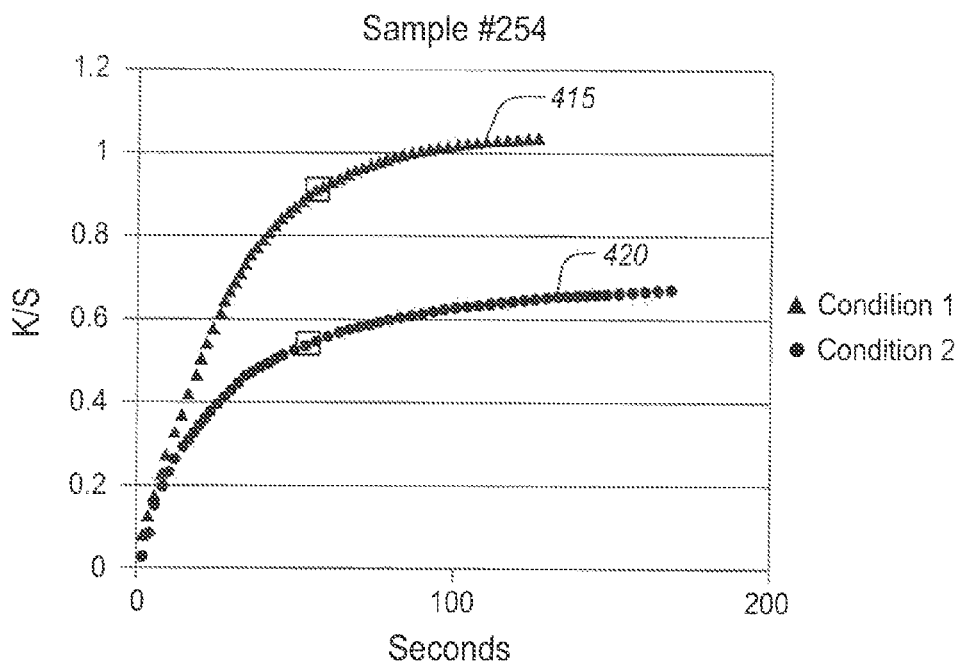
FIGS. 4a and 4b show kinetic charts in terms of K/S of strips tested with two different blood donors, Condition 1 is control with Triton X-100, while condition 2 is experimental test strips containing P123 and Triton X-100.
Figure 4B:
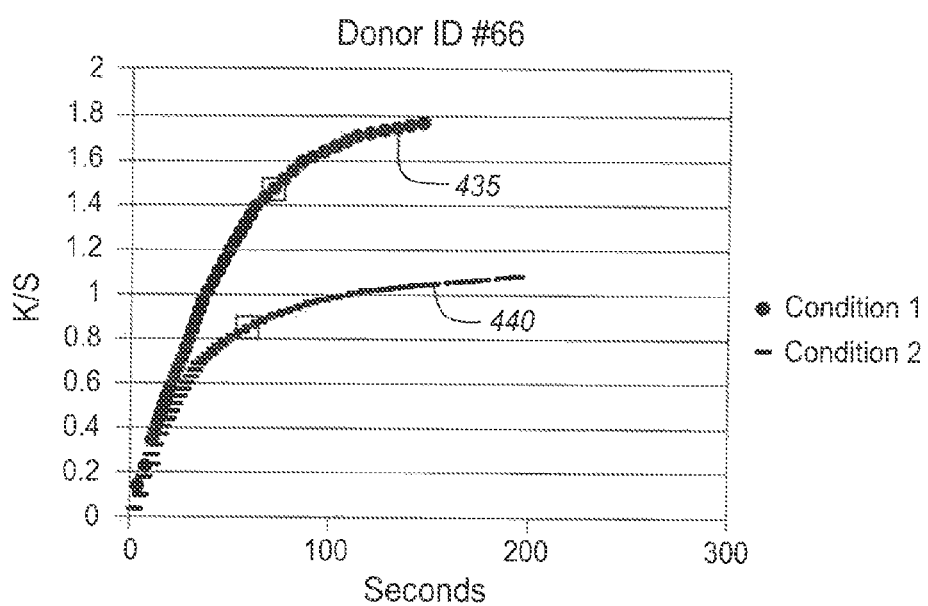

Finally, whole blood was tested to determine if the matrix of blood would disrupt the function of P123 and TX100. Color was reduced, and the K/S values of the P123 strips between the two blood samples was proportional to the amount of non-LDL in the native blood samples. FIGS. 4a-4b show kinetic charts of strips tested with two different blood donors, sample #254 and donor ID #66. Condition 1, 415, 435 represents the control; and Condition 2, 420, 440 represents the strips containing P123. For this test, the meter endpoint was extended to a 0.01% R change every two seconds in order to observe a complete kinetic reaction. The red data point indicates a typical meter endpoint which uses a <0.2% change in reflectance as reaction progress.

Data from the whole blood testing showed that a reproducible method of differentiating LDL from non-LDL is possible in a dry strip format. For this test, the meter endpoint was extended to a 0.01% R change every two seconds in order to observe a complete kinetic reaction. The red data point indicates a typical meter endpoint which uses a <0.2% change in reflectance as reaction. This was done to confirm that the kinetic profile of non-LDL is moving to completion.

Success criteria in a dry test strip was the highest level of formulary selectivity preference for HDL, e.g., a 5:1 (HDL: LDL) ratio indicates a high level of HDL selectivity. Thus, as seen in the table below, the ratio 20:1 of P123:Trition X-100 gave the desired selectivity.

Figure 7:
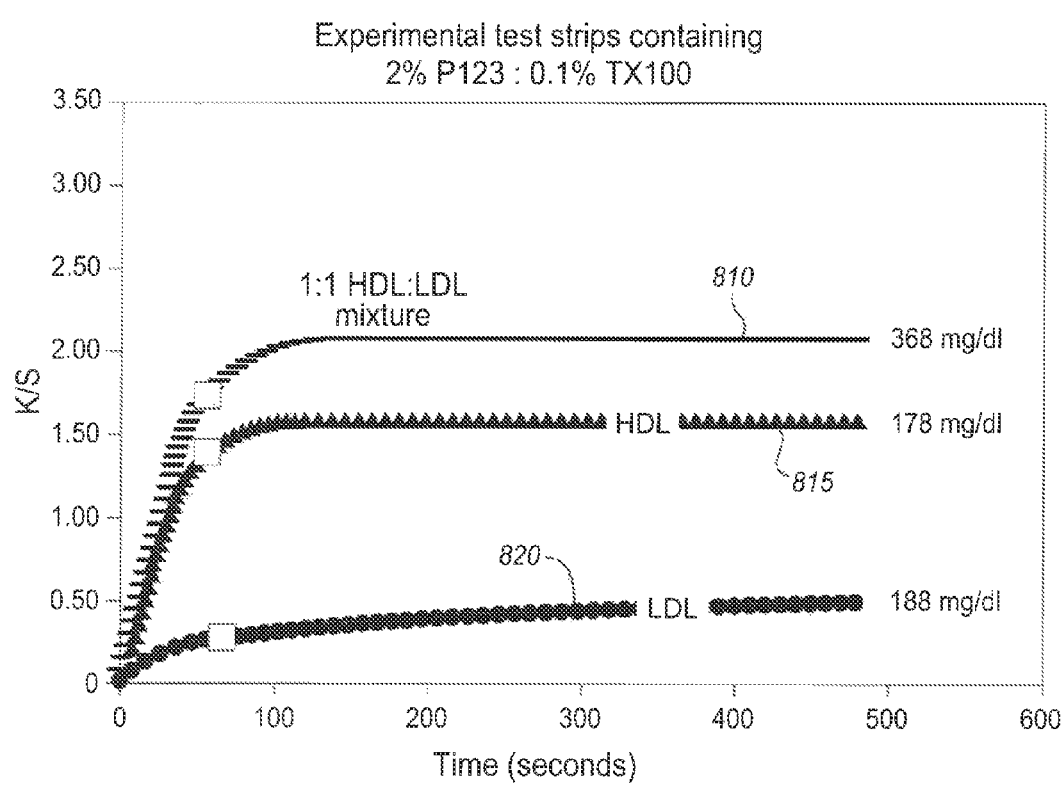
FIG. 7 shows a control test of a current Polymer Technology Systems, Inc. (PTS), reaction layer including 2% P123 and 0.1% Triton X-100.

FIG. 7 shows an experimental test strip including a current Polymer Technology Systems, Inc. (PTS), reaction layer, containing 2% P123 and 0.1% Triton X-100, with trendline 810 representing a mixture of LDL and HDL, line 815 representing HDL, and line 820 representing LDL. Good suppression of LDL is observed with 5:1 HDL:LDL selectivity, with the mixture consisting of both LDL and HDL fractions in equal concentrations giving a similar value to the total HDL fraction.

Previous studies so far described the first foray into dry strip technology, capturing the kinetics of the reaction means of quantification and demonstrating the potential of the chemistry.

The advance into dry strip chemistry looked very promising, but results could no longer be quantified with lipoprotein fractions and reaction kinetics. Using fresh serum samples, strips containing P123/Triton X-100 were correlated to non-LDL obtained on a clinical chemistry analyzer, obtaining a calibration curve to set each data point to a non-LDL value. Each data point then was subtracted from the Integra determined total cholesterol to give a "Measured LDL" value. Correlating the measured LDL value to the Integra Direct LDL value gave an indication of any bias in the non-LDL assay.

TABLE 4

Lists the correlation results from three different P123 concentrations at three different pH levels.

| Condition | Non-LDL $R^2$ | Non-LDL v K/S equation | LDL equation | LDL $R^2$ |
|---|---|---|---|---|
| pH 5.4; 1% P123 | 0.6212 | y = 0.0183x + 0.119 | y = 0.7731x + 30.224 | 0.8729 |
| pH 5.4; 2% P123 | 0.661 | y = 0.0159x + 0.1843 | y = 0.7662x + 31.028 | 0.9041 |
| pH 5.4; 3% P123 | 0.6511 | y = 0.0165x − 0.0285 | y = 0.7941x + 27.424 | 0.8882 |
| pH 6.8; 1% P123 | 0.8017 | y = 0.0163x − 0.0632 | y = 0.8533x + 19.451 | 0.9544 |
| pH 6.8; 2% P123 | 0.8503 | y = 0.0126 + 0.025 | y = 0.86x + 19 | 0.9736 |
| pH 6.8; 3% P123 | 0.8253 | y = 0.0108x − 0.0231 | y = 0.8612x + 18.517 | 0.9625 |
| pH 7.4; 1% P123 | 0.7916 | y = 0.0105x + 0.0206 | y = 0.813x + 24.918 | 0.9635 |
| pH 7.4; 2% P123 | 0.7182 | y = 0.0099x + 0.0193 | y = 0.7707x + 30.691 | 0.9418 |
| pH 7.4; 3% P123 | 0.8278 | y = 0.0098x − 0.0368 | y = 0.8553x + 19.841 | 0.9661 |

TABLE 3

Selecting the ratio of P123 to Triton X-100.

| P123:Triton X-100 Ratios and Concentrations | HDL:LDL Selectivity |
|---|---|
| 10:1 | |
| 0.5%:0.05% | 2.29 |
| 1%:0.1% | 3.62 |
| 2%:0.2% | 3.72 |
| 15:1 | |
| 0.75%:0.05% | 4.95 |
| 1.5%:0.1% | 3.69 |
| 3%:0.2% | 3.50 |
| 20:1 | |
| 1%:0.05% | 3.56 |
| 2%:0.1% | 5.11 |
| 4%:0.2% | 4.00 |

A pH study coupled with changing P123 concentration at 10:1 constant P123: Triton X-100 ratio was tested with serum to examine any dependencies. All nine conditions were tested on the same day with 12 different serum samples, once across five meters.

From the above data, it is clear P123 provides some selectivity for non-LDL. A pH of 5.4 seems less desirable, as the non-LDL curves look very similar to a total cholesterol test strip; and a pH of 7.4 also appears to be less linear than strips at pH 6.8. Among the pH 6.8 strips, 1% P123 comes in last in terms of both precision and LDL bias. 2% P123 had a better R2 than 3%, but the strips containing 3% P123 had a slightly lower LDL bias. The slope of the final LDL equation, indicating the level of bias in the assay, suggests that some LDL still interacts with the non-LDL strips.

Therefore, combinations of Triton X-100 and $POE_X$-$POP_Y$-$POE_X$ for use in test strips have been determined to be operable from a pH from approximately 5.4 to approximately 8. Optionally, the pH is from 6 to 7.5. Optionally, the pH is at 6.8. Therefore, combinations of Triton X-100 and POE$_X$-POP$_Y$-POE$_X$ for use in test strips have been determined to be in a ratio of 0.1% Triton X-100 to between 0.5% to 5% POE$_X$-POP$_Y$-POE$_X$. Optionally, the ratio is 0.1% Triton X-100 to between 1% to 3% POE$_X$-POP$_Y$-POE$_X$. Optionally, the ratio is 0.1% Triton X-100 to 2% POE$_X$-POP$_Y$-POE$_X$. In some embodiments, P123 is chosen for the various combinations of pH and Triton X-100.

It is noteworthy to mention that, during the course of scientific investigation, it was determined that a new borosilicate glass fiber membrane D-23 from IW Treamont impregnated with Phaseolous Vulgaris Lectins PHA-P performed better than the non-woven Tuffglass (Alhstrom 144) from Pall.

It was the aim going forward to increase the agreement (slope) and bring it in close to unity or between the 0.90 to 1.10 range as compared LDL values obtained on Roche LDL C+ and decrease the intercept preferably to ≤5 mg/dL.

In some alternatives, the slope of the curve is improved by precipitating a portion of the LDL prior to the mobilization of the non-LDL cholesterols. This enables the P123/TX100 system and the LDL curve to surpass 0.9× for the slope, which was considered desirable for a successful assay. Although, many chemistries may be used for pre-precipitation of LDL, dextran sulfate is chosen in some embodiments. In some embodiments, polyvinylsulfate may be used to precipitate LDL prior to the treatment of Triton X-100 and POE$_X$-POP$_Y$-POE$_X$ described above.

Early LDL assays by Boehringer Mannheim (polyvinylsulfate) and Immuno AG (dextran sulfate) utilized polyanion precipitation to precipitate LDL and measure the difference in total cholesterol before and after precipitation. Siekmeir, Rudiger, *Clinical Chemistry*, 1990; 36(12):2109-2113, investigates the reliability of these assays and correlation to beta quantification. Both assays suffered from some VLDL coprecipitation at the polyanion concentrations needed to precipitate all of the LDL in the sample, with the dextran sulfate method precipitating less VLDL.

While the above methods alone are not sufficient for an accurate LDL assay, trace amounts of polyanions is utilized to remove some of the LDL but at low enough concentrations to leave the VLDL intact. The idea behind this is that the LDL particles could be lowered before reacting with the non-LDL reaction membrane, reducing the amount of LDL the non-LDL membrane has to exclude. Too much polyanion (dextran sulfate, for example) kills the selectivity for LDL.

The first step into this approach required an experiment demonstrating that some LDL could be precipitated without affecting the non-LDL. Dextran sulfate of MW 5K, 10K, 50K, and 500K was tested with 150 mM MgCl$_2$, with 500K dextran sulfate identified as the most appropriate.

TABLE 5

The results from 20 parts of an LDL fraction combined with 1 part of a DS reagent (saline for Control)

| Ratio (LDL Fraction:Reagent) | | Integra TC (mg/dL) | Integra HDL (mg/dL) | Integra LDL (mg/dL) | VLDL (TC-HDL-LDL) |
|---|---|---|---|---|---|
| 20:1 | Control (Saline) | 216.5 | 2.1 | 171.9 | 42.5 |
| | 0.15% 500K Dextran Sulfate/150 mM MgCl | 179.9 | 1.9 | 134.9 | 43.1 |

Immediately after reagent addition, samples were centrifuged and the supernatant was tested on the Integra for total cholesterol, HDL, and LDL.

Table 5 shows that the LDL concentration was lowered without affecting the VLDL or HDL concentration. The results from screening dextran sulfate led to the belief that approximately 20% of LDL could be removed from a sample before precipitation of any non-LDL.

A variety of dextran sulfate (DS) with MW 5K; 50K; 500K; >500K was tested along side with a wide range of MgCl$_2$ concentrations. Most of the testing was performed as a reagent on Cobas Integra 400+ to identify the optimal concentration. A stock solution of dextran sulfate with molecular weight of 500K at 0.15% w/v with 150 mM MgCl$_2$ was tested to determine at what point only LDLs are precipitated.

The table 6 below shows that 20 parts of saline containing a fixed level of LDL fraction mixed with 1 part of the stock resulted as the preferred combination. The concentration of LDL was lowered by ~33 mg/dL, while keeping VLDL concentration virtually unchanged at 43.3 mg/dL when compared to the aliquot of the same sample treated with saline as Control (see highlighted row). This demonstrates that at least some amount of LDL has been precipitated in the presence of VLDL without affecting VLDL concentration.

TABLE 6

Effects of various concentrations of dextran sulfate.

| Stock Concentration of Dextran Sulfate/MgCl$_2$ | LDL:Stock DS/MgCl$_2$ Ratio | Final DS/Mg$^{+2}$ Concentration | Description of the test | TC (mg/dL) | HDL (mg/dL) | LDL (mg/dL) | VLDL (TC − HDL − LDL) (mg/dL) |
|---|---|---|---|---|---|---|---|
| 0.15% DS/150 mM MgCl$_2$ | 1:1 | 0.075% DS/75 mM MgCl$_2$ | Control (Saline) | 117.3 | 3 | 93.5 | 20.8 |
| | | | Reagent | 1 | 0 | 0 | 1 |
| 0.15% DS/150 mM MgCl$_2$ | 5:1 | 0.025% DS/25 mM MgCl$_2$ | Control (Saline) | 192.2 | 2.3 | 153.5 | 36.4 |
| | | | Reagent | 0.9 | 0.2 | 0 | 0 |
| 0.15% DS/150 mM MgCl$_2$ | 10:1 | 0.014% DS/13.64 mM MgCl$_2$ | Control (Saline) | 216.2 | 2.2 | 173.1 | 40.9 |
| | | | Reagent | 49.7 | 2 | 35.5 | 12.2 |
| 0.15% DS/150 mM MgCl$_2$ | 20:1 | 0.007% DS/7.14 mM MgCl$_2$ | Control (Saline) | 229.5 | 1.9 | 182.2 | 45.5 |
| | | | Reagent | 194.3 | 2.2 | 148.8 | 433 |
| 0.15% | 50:1 | 0.0029% | Control | 231.5 | 2.1 | 187.9 | 41.5 |

TABLE 6-continued

Effects of various concentrations of dextran sulfate.

| Stock Concentration of Dextran Sulfate/MgCl$_2$ | LDL:Stock DS/MgCl$_2$ Ratio | Final DS/Mg$^{+2}$ Concentration | Description of the test | TC (mg/dL) | HDL (mg/dL) | LDL (mg/dL) | VLDL (TC − HDL − LDL) (mg/dL) |
|---|---|---|---|---|---|---|---|
| DS/150 mM MgCl$_2$ | | DS/2.94 mM MgCl$_2$ | (Saline) Reagent | 237.6 | 1.6 | 185.1 | 50.9 |

Due to the instantaneous interaction of dextran sulfate/MgCl$_2$ with LDL, the best layer to place it in for LDL precipitation and removal was the Cytosep. Impregnation of Cytosep 1660 with 0.15% dextran sulfate (MW 500K) with 150 mM MgCl$_2$ were placed in strips above the non-LDL reaction membrane containing P123: Triton X-100. Testing with whole blood samples gave excellent final correlations to LDL. This indicates that a similar plasma to Dextran sulfate/MgCl$_2$ interaction ratio is maintained or exists in the test strip as that observed in test samples highlighted below.

Figure 8A:
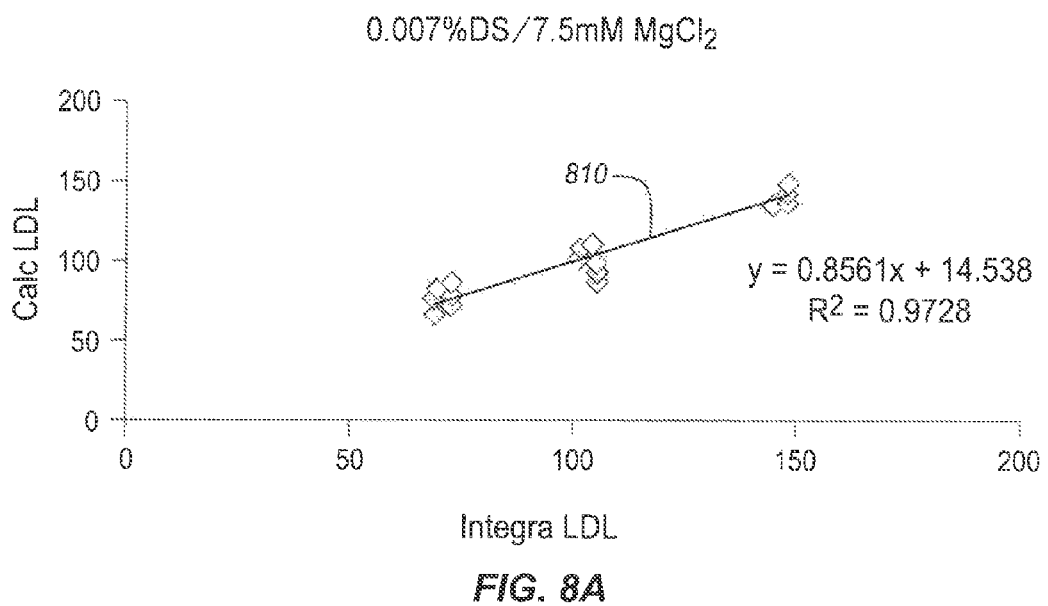
FIGS. 8a-8d show concentration testing for various combinations of dextran sulfate.
Figure 8B:
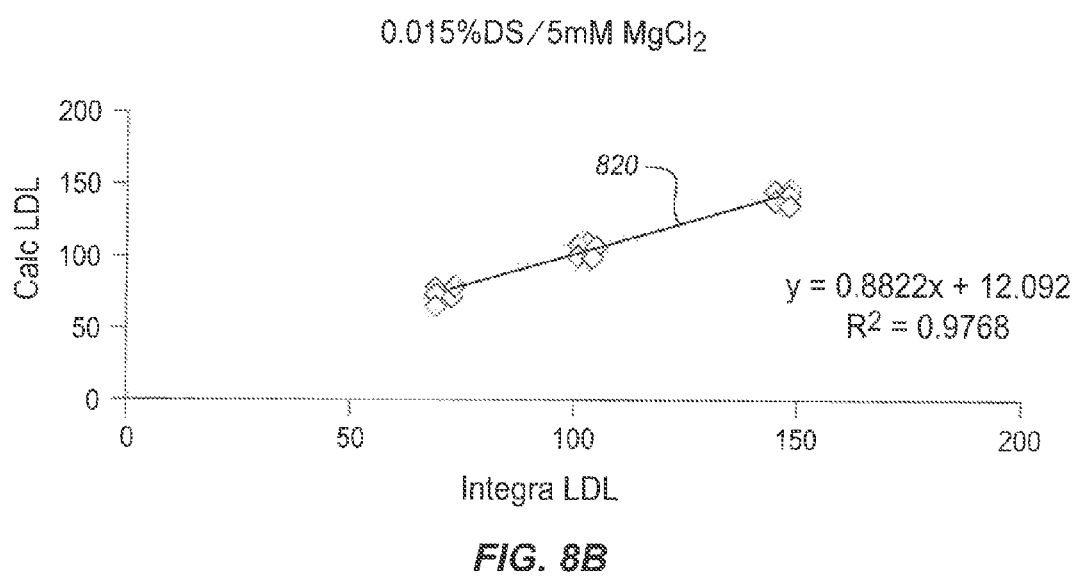
Figure 8C:
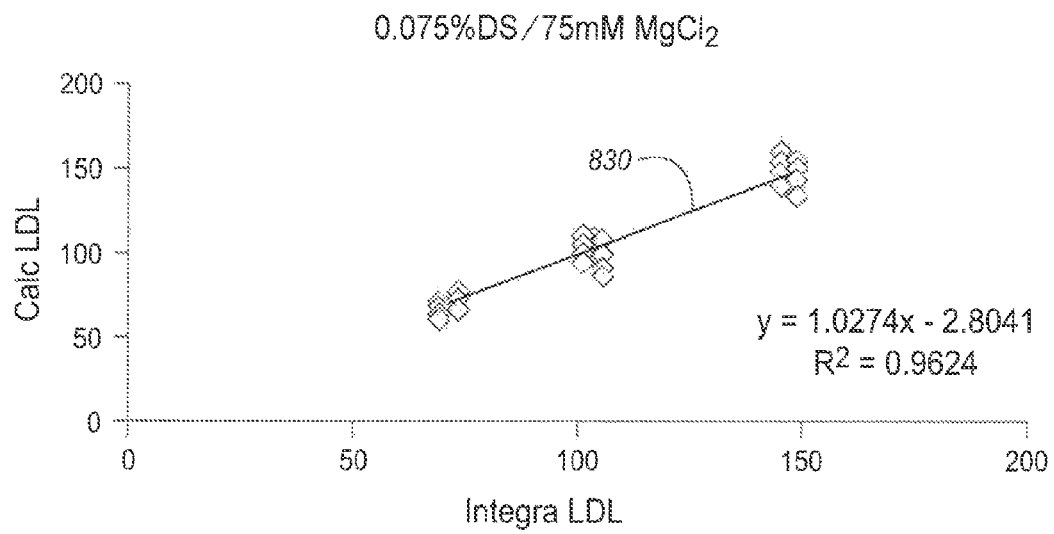
Figure 8D:
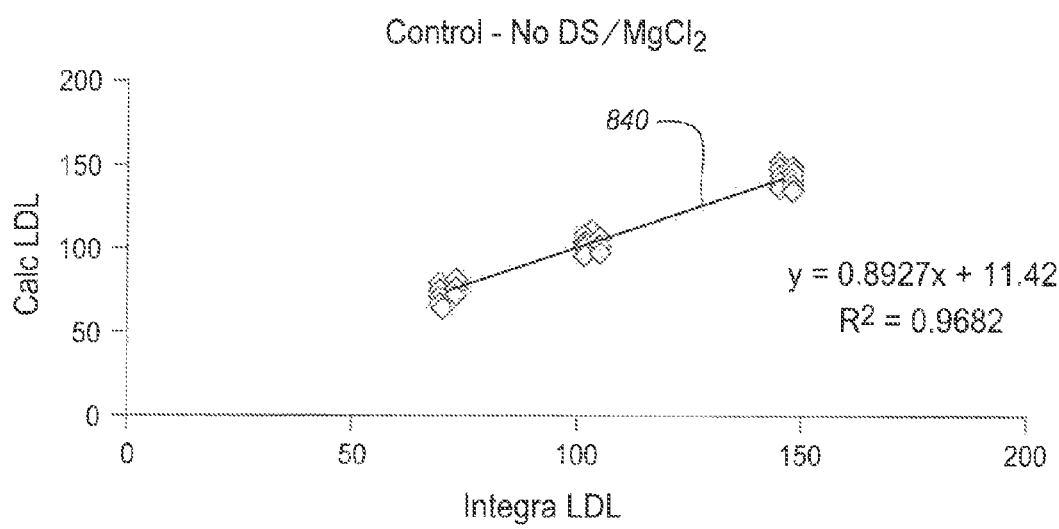

A titration study was performed using LDL fractions at known concentrations to identify the levels of dextran sulfate/MgCl$_2$ concentration in a test strip. Three concentrations were tested: i) 0.007% DS/7.5 mM MgCl$_2$, FIG. 8a, trend line 910; ii) 0.015% DS/15 mM MgCl$_2$, FIG. 8C, trend line 930; and iii) 0.075% DS/75 mM MgCl$_2$ FIG. 8B, trend line 920; in a test strip containing the non-LDL cholesterol membrane alongside a Control. The Control strip contained the non-LDL reaction membrane but without the dextran sulfate/MgCl$_2$ in Cytosep1660, FIG. 8D, trend line 940. The correlations below show that only 0.075% DS/75 mM MgCl$_2$ displayed a good correlation and agreement with the Integra LDL. However, this concentration had to be doubled when testing with whole blood.

Dextran sulfate/Mg+2 titration revealed that 0.15% dextran sulfate is ideal for serum samples. The cytosep contains 0.15% dextran sulfate/150 mM MgCl and sits on top of a P123/TX100 reaction membrane.

Figure 5A:
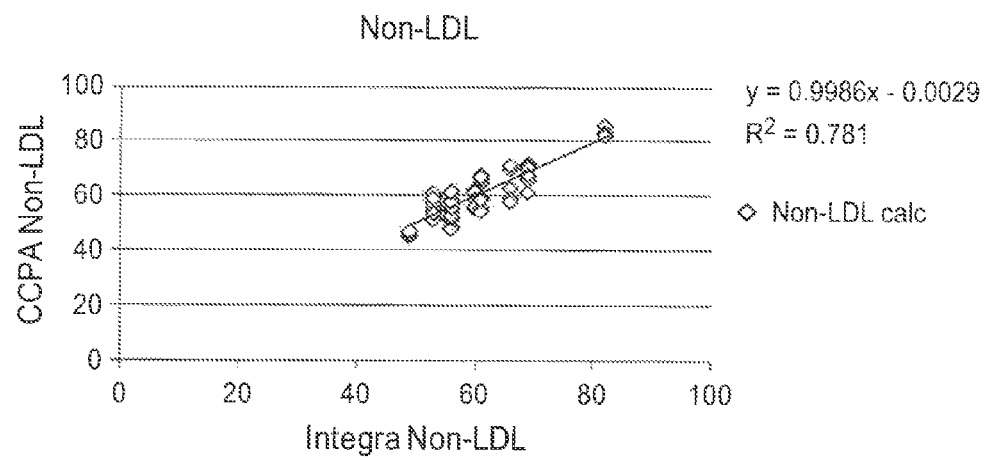
FIGS. 5a-5h show graphs of tests with P123 and Triton X-100 showing that the only correlations to various analytes.
Figure 5B:
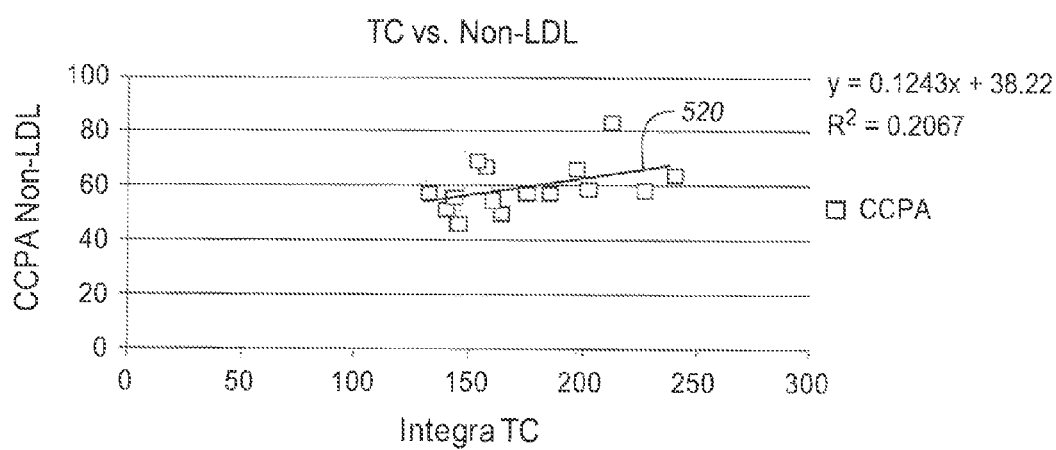
Figure 5C:
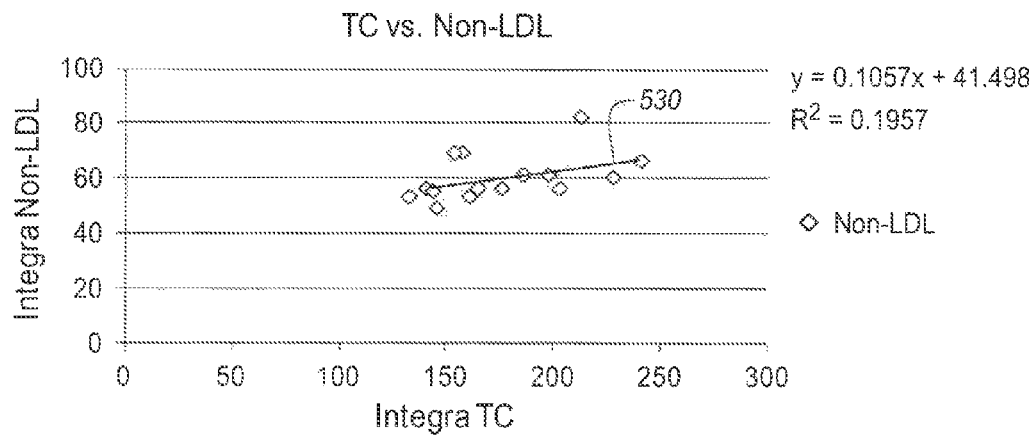
Figure 5D:
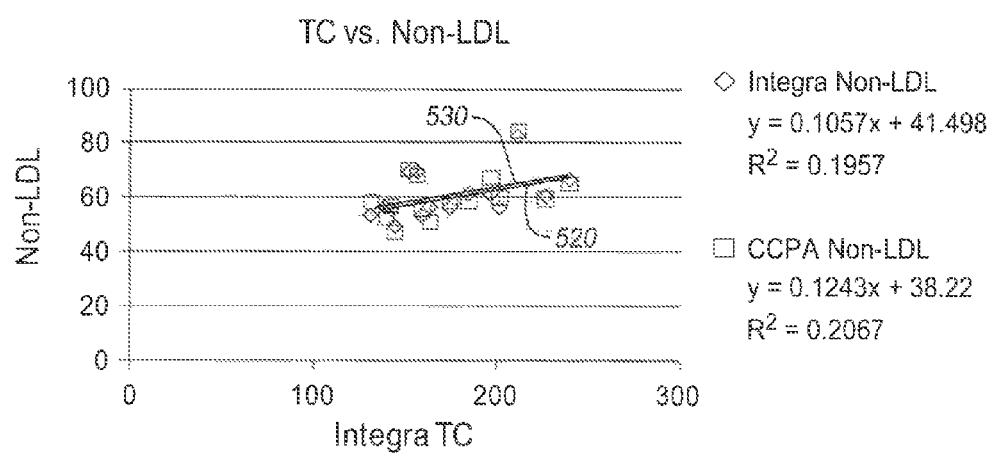
Figure 5E:
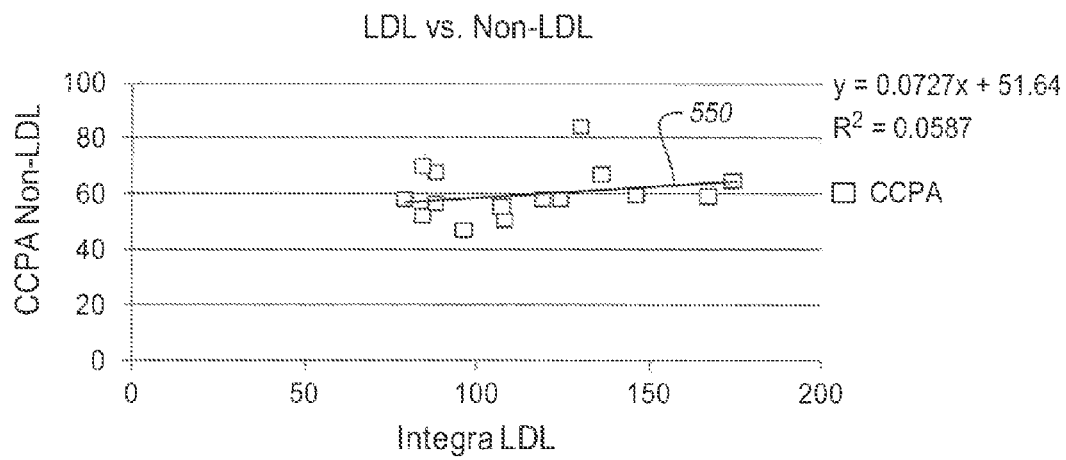
Figure 5F:
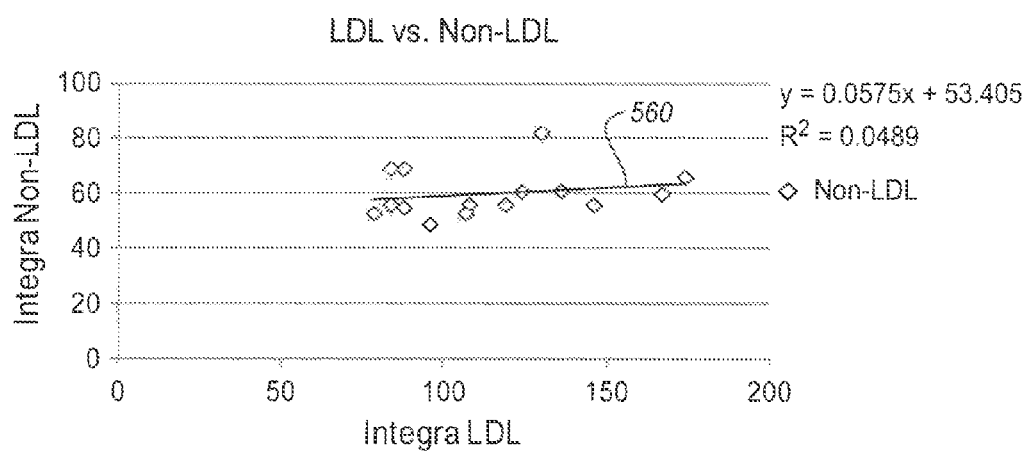
Figure 5G:
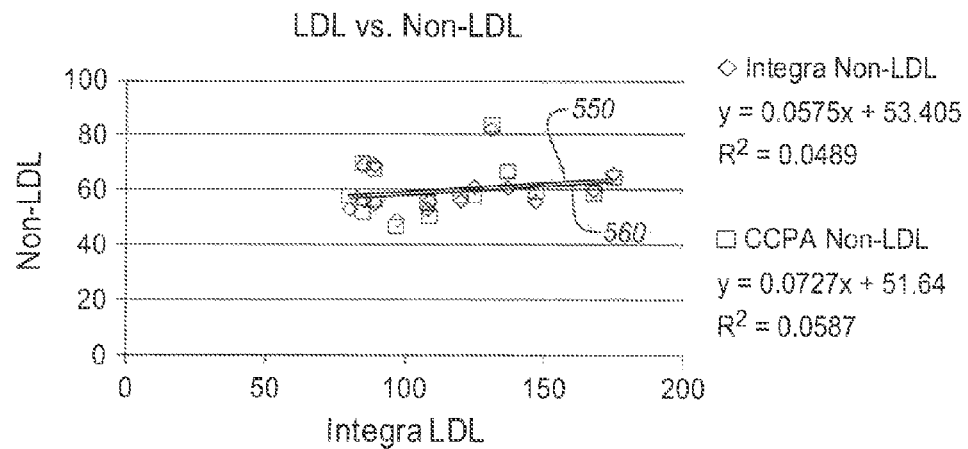

The graphs in FIGS. 5a-5h show that the only correlation is to non-LDL. In FIG. 5a, the graph shows the amount of non-LDL determined according to the methods described herein as compared to the Integra non-LDL amount determined according to industry accepted techniques. The term Integra in this case is used to refer to the measurement of the selected analyte using the Integra 917, Modula P and Cobas Integra 400+. Trend line 510 shows the correlation to the accepted standard is high. FIG. 5B and trend line 520 shows the relationship between non-LDL according to the methods described herein as compared to an Integra total cholesterol. FIG. 5B should be contrasted with 5C showing an Integra non-LDL measurement compared to an Integra Total Cholesterol (trend line 530). In both cases the correlation is low and very similar, showing that both the Integra non-LDL and the non-LDL according to the methods described herein are similarly not correlated to total cholesterol. FIG. 5D shows a combined graph of trend lines 520, 530 for comparison. FIG. 5E and trend line 550 shows the relationship between Non-LDL according to the methods described herein as compared to an Integra LDL. FIG. 5E should be contrasted with 5F showing an Integra non-LDL measurement compared to an Integra LDL (trend line 560). In both cases the correlation is low and very similar, showing that both the Integra non-LDL and the non-LDL according to the methods described herein are similarly not correlated to LDL. FIG. 5G shows a combined graph of trend lines 550, 560 for comparison.

Figure 5H:
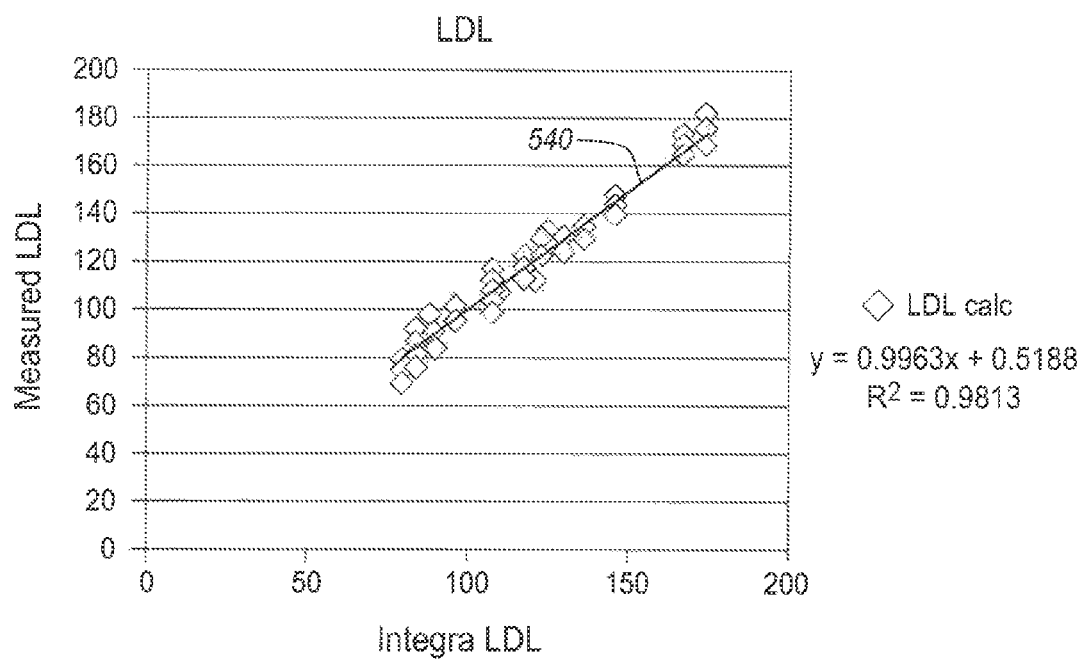

The final LDL curve in FIG. 5h looks excellent, as there is no LDL bias (0.99 slope) to the Integra and correlation is very good ($R^2$=0.9813). This compares the LDL according to the techniques presented herein to Integra LDL measurements. Trend line 540 shows a very high correlation. As a control, when the same selectivity membrane was placed in conjunction with a total cholesterol reaction membrane (which only consists of Triton X-100), no correlation to non-LDL was observed, indicating that P-123 in the non-LDL reaction membrane plays a very important role.

In other words, trendline 520 shows the correlation of non-LDL to total cholesterol. Trendlines 520 and 550 show virtually no correlation to total cholesterol and LDL respectively. In FIG. 5h, trendline 540 shows the correlation between the measured LDL from an integra LDL measurement and the measured LDL from the embodiment of the test described herein and in the immediately previous paragraphs. As is clear, there is a very high correlation, almost 1 to 1, suggesting that the resulting methodology is highly accurate.

The final LDL curve in FIG. 5h looks excellent, as there is no LDL bias (0.99 slope) to the Integra and correlation is very good ($R^2$=0.9813). As a control, when the same selectivity membrane was placed in conjunction with a total cholesterol reaction membrane (which only consists of Triton X-100), no correlation to non-LDL was observed, indicating that P-123 in the non-LDL reaction membrane plays a very important role.

Figure 6:
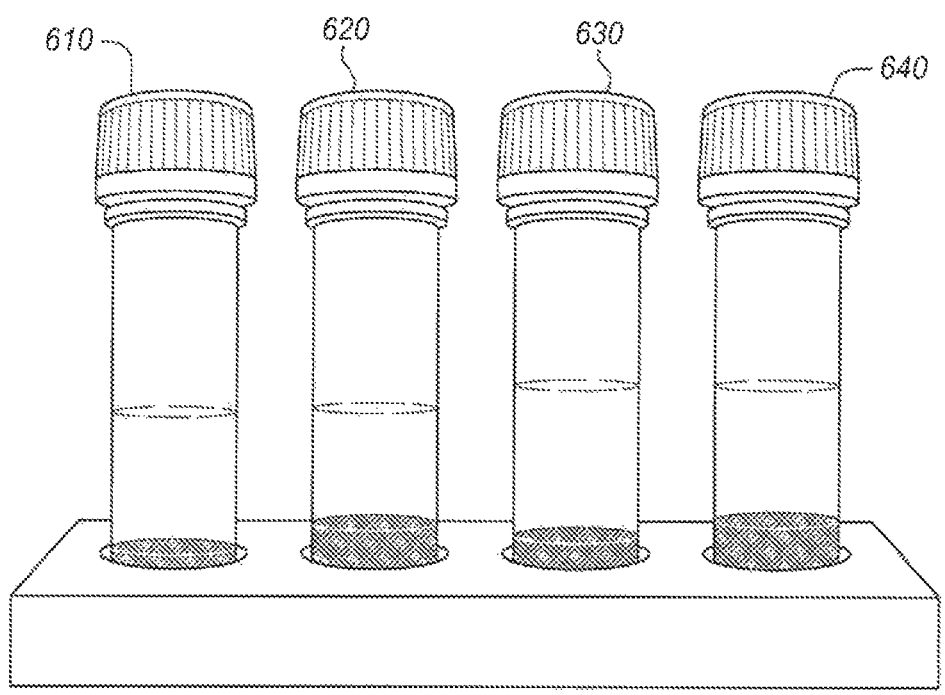
FIG. 6 shows the non-hemolytic properties of P123 and Triton X-100 mixture.

Before whole blood testing could begin, the effects of the surfactants on hemolysis were considered. It is well known that Triton X-100 is very hemolytic, which in part necessitates the need for a good blood separation membrane. FIG. 6 demonstrates that P123 is not hemolytic and prevents any hemolytic activity when combined with Triton X-100, with tube 610 representing results of whole blood in saline, tube 620 representing results of whole blood in 0.1% Triton X-100, tube 630 representing results of whole blood in 2% P123, tube 640 representing results of whole blood in 0.1% Triton X-100 and 2% P123, and whole blood combined with saline, TX100, P123, or a mixture thereof. It can clearly be observed that P123 is not hemolytic and prevents any hemolytic activity when combined with TX100.

The hemolysis data is exciting, as it demonstrates the non-obvious change in TX100 properties when combined with P123. The lack of any increased hemolysis over TX100 allowed for testing with whole blood without fear of increased hemolysis error.

Whole blood testing was continued on experimental test strips on four different occasions. The table below summarizes the output of the calibration curves and final correlation to the LDL analyte.

TABLE 7

Table comparing the results of four different
series of whole blood testing.

| Entry | Non-LDL $R^2$ | Non-LDL v K/S equation | LDL equation | LDL $R^2$ |
|---|---|---|---|---|
| 1 | 0.8548 | Y = 0.01x − 0.1826 | Y = 0.9629x + 4.2732 | 0.9802 |
| 2 | 0.5979 | Y = 0.0102x − 0.2011 | Y = 0.9313x + 6.897 | 0.9529 |
| 3 | 0.9333 | Y = 0.0098x − 0.1936 | Y = 0.973x + 3.3117 | 0.9765 |
| 4 | 0.874 | Y = 0.0104x − 0.2372 | Y = 0.9835x + 0.9834 | 0.9203 |

All strips consisted of the format described below.

The data for whole blood looks excellent in terms of LDL bias and correlation. One can conclude from the preceding data that a successful non-LDL strip to compute LDL from a reliable total cholesterol assay has been produced in the following format:

| | |
|---|---|
| Blood Spreading Layer | Petex |
| Blood Separation layer | D-23 Brosilicate glass fiber with *phaselous vulgaris* lectins |
| Secondary Blood Separation Layer | Cytosep (0.15% Dextran Sulfate/150 mM MgCl) |
| Reaction Membrane | Non-LDL Reaction Membrane (3% P123/0.2% TX100) |

It is important to note that this architecture in a single-analyte strip is at a proof-of-concept stage. In the final development stage, the non-LDL assay would sit in a panel with at least cholesterol and another analyte as shown below.

| Layer | Total Cholesterol | LDL | Any analyte |
|---|---|---|---|
| Blood Spreading Layer | Polyether Sulfone (PES) 18/13 TW Hyphil | | |
| Blood Separation layer | D-23 Borosilicate glass fiber with Lectins | | |
| Secondary Blood Separation Layer | Cytosep 1660 | LDL selectivity Membrane | corresponding |
| Reaction Membrane | Total Cholesterol Reaction Membrane | Non-LDL Reaction Membrane | Reaction Membrane for an analyte |
| Adhesive | | Adhesive | |

It should also be noted that each LDL curve seen in this report has been computed by subtracting the non-LDL value from the Integra total cholesterol assay. Substantial work needs to be completed to develop the best non-LDL assay, such as determining preparation methods, interferents, and stability. However, the initial chemistry reaction with non-LDL has been proven to work in a single analyte strip format. If the chemistry works in this format, it is a logical conclusion that it can be placed into a panel format with a Polymer Technology Systems, Inc. (PTS), cholesterol assay to give a simple LDL assay correlating well to the Integra direct LDL assay.

While specific embodiments have been described in detail in the foregoing detailed description and illustrated in the accompanying drawings, it will be appreciated by those skilled in the art that various modifications and alternatives to those details could be developed in light of the overall teachings of the disclosure and the broad inventive concepts thereof. It is understood, therefore, that the scope of this disclosure is not limited to the particular examples and implementations disclosed herein but is intended to cover modifications within the spirit and scope thereof as defined by the appended claims and any and all equivalents thereof.

Note that, although particular embodiments are shown, features of each attachment may be interchanged between embodiments.

What is claimed as new and desired to be protected by Letters Patent of the United States is:

1. A method of measuring LDL cholesterol from a human subject providing a blood sample, the blood sample including chylomicrons, the method comprising:
    providing a dry test strip;
    receiving the blood sample at the dry test strip;
    separating red blood cells from the blood sample in a first layer of the dry test strip;
    reacting all non-LD cholesterol including chylomicrons in the blood sample in a reaction layer;
    producing a color change proportional to the non-LDL cholesterol;
    measuring the color change to determine a non-LDL cholesterol amount in the blood sample; and
    subtracting the non-LDL cholesterol amount from a total cholesterol amount in the blood sample to yield an LDL cholesterol amount for the blood sample wherein specificity of the reacting non-LDL cholesterol in the blood sample, due to a chemistry that solubilizes all cholesterols, including chylomicrons, other than LDL in the reaction layer, is such that accuracy is not substantially negatively affected by the presence of chylomicrons.

2. The method of claim 1, wherein the blood sample is from an individual who has not fasted, and the resulting LDL cholesterol amount is more accurate than the Friedwald equation.

3. The method of claim 1, wherein the reaction layer further includes a surfactant and a reflectivity changing reactant, wherein the reacting includes solubilizing essentially only cholesterol from non-LDL analytes, the cholesterol from non-LDL analytes reacting with the reflectivity changing reactant in order to change a reflectivity of the blood sample.

4. The method of claim 1, wherein the reaction layer includes a POE-POP-POE block copolymer.

5. The method of claim 4, wherein the POE-POP-POE block copolymer is selected from the list of copolymers consisting of a copolymer having a MW 3800, and a formula $POE_7\text{-}POP_{54}\text{-}POE_7$; a copolymer having a MW 4400, and a formula $POE_5\text{-}POP_{68}\text{-}POE_5$; a copolymer having a MW 5750, and a formula $POE_{20}\text{-}POP_{70}\text{-}POE_{20}$; and a copolymer having a MW 12600; and a formula $POE_{106}\text{-}POP_{70}\text{-}POE_{106}$.

6. The method of claim 1, further comprising:
    spreading the blood sample with a spreading layer, oriented on top of the first layer.

7. The method of claim 6, further comprising:
    reacting the blood sample in a total cholesterol reaction layer, the total cholesterol reaction layer oriented to receive a portion of the blood sample from the spreading layer;
    producing a color change proportional to the total cholesterol; and
    measuring a color change to determine the total cholesterol amount in the blood sample.

8. The method of claim 1, wherein the test strip includes a secondary blood separation layer adjacent to the red blood cell separation first layer, the secondary blood separation layer separating additional red blood cells from the blood sample, where the secondary blood separation layer further includes dextran sulfate.

9. The method of claim 1, wherein the first layer includes D-23 borosilicate glass fiber impregnated with Phaselous Vulgaris (PHA-P) Lectins.

10. The method of claim 1, wherein chemistry that solubilizes all cholesterols other than LDL in the reaction layer includes a surfactant and a POE-POP-POE block copolymer.

11. The method of claim 10 wherein the POE-POP-POE block copolymer is a copolymer having a MW 5750, and a formula $POE_{20}$-$POP_{70}$-$POE_{20}$.

12. The method of claim 11, further comprising: removing a portion of LDL from the blood sample in an initial incomplete precipitation step.

13. The method of claim 12, wherein Dextran Sulfate/Mg+2 is added to the test strip to provide for the removing a portion of LDL from the blood sample.

* * * * *